United States Patent [19]

Lacoste et al.

[11] Patent Number: 5,170,790
[45] Date of Patent: Dec. 15, 1992

[54] ARM HAVING AN END MOVABLE IN TRANSLATION, AND THERAPEUTIC TREATMENT APPARATUS CONSTITUTING AN APPLICATION THEREOF

[75] Inventors: Francois Lacoste, Lyons; Marian Devonec, Miribel; Muriel Cathaud, Venissieux, all of France

[73] Assignee: Technomed International, Paris, France

[21] Appl. No.: 679,701

[22] Filed: Apr. 3, 1991

[30] Foreign Application Priority Data

Apr. 6, 1990 [FR] France ................. 90 04440

[51] Int. Cl.$^5$ ............................................. A61B 10/00
[52] U.S. Cl. ............................ 138/660.01; 128/122.1;
  128/660.09; 128/662.03
[58] Field of Search .......................... 33/438, 441;
  128/660.01, 660.04, 660.07, 660.09, 662.03,
  122.1; 73/861.25, 861.26

[56] References Cited

U.S. PATENT DOCUMENTS

| | | | |
|---|---|---|---|
| 2,202,195 | 5/1940 | Drachman et al. | 128/122.1 |
| 2,915,828 | 12/1959 | Baumbach | 33/441 |
| 4,381,787 | 5/1983 | Hottinger | 128/660.07 |
| 4,399,822 | 8/1983 | Theumer | 128/660.09 |
| 4,431,007 | 2/1984 | Amazeen et al. | 128/660.04 |
| 4,543,959 | 10/1985 | Sepponen | 128/660.04 |
| 4,817,621 | 4/1989 | Aaslid | 128/662.03 |

FOREIGN PATENT DOCUMENTS 6403232 9/1965 Netherlands ............ 128/122.1

OTHER PUBLICATIONS

W. B. Taylor, J. W. Hunt, F. S. Foster, R. Blend, A. Worthington; "A High-Resolution Transrectal Ultrasonographic System", Ultrasound in Med. & Biol. vol. 5, No. 2, 1979, pp. 129-131, 133-138 and FIG. 3.

Primary Examiner—Kyle L. Howell
Assistant Examiner—George Manuel
Attorney, Agent, or Firm—Cohen, Pontani, Lieberman, Pavane

[57] ABSTRACT

A positioning device for positioning an instrument in three dimensions, the device comprising at least one arm which is essentially rigid having a first end and a second end, the second end being hinged relative to a support stand via at least one hinge axis, and said instrument being mounted on a support which is connected to the second end of the arm via at least one hinge axis, wherein said instrument comprises an exploration probe and said support for the instrument comprises a device for motion in translation enabling the instrument comprising the exploration probe to be moved in translation relative to the second end of the arm, making it possible to perform exploration for each of the translation positions. The invention enables the instrument at the end of the positioning device to be moved in translation, thereby providing a maximum amount of freedom for positioning the instrument in three dimensions and facilitating locating operations, particularly in the context of transrectal echographic location, this being particularly useful for therapeutic treatment of the prostate.

20 Claims, 4 Drawing Sheets

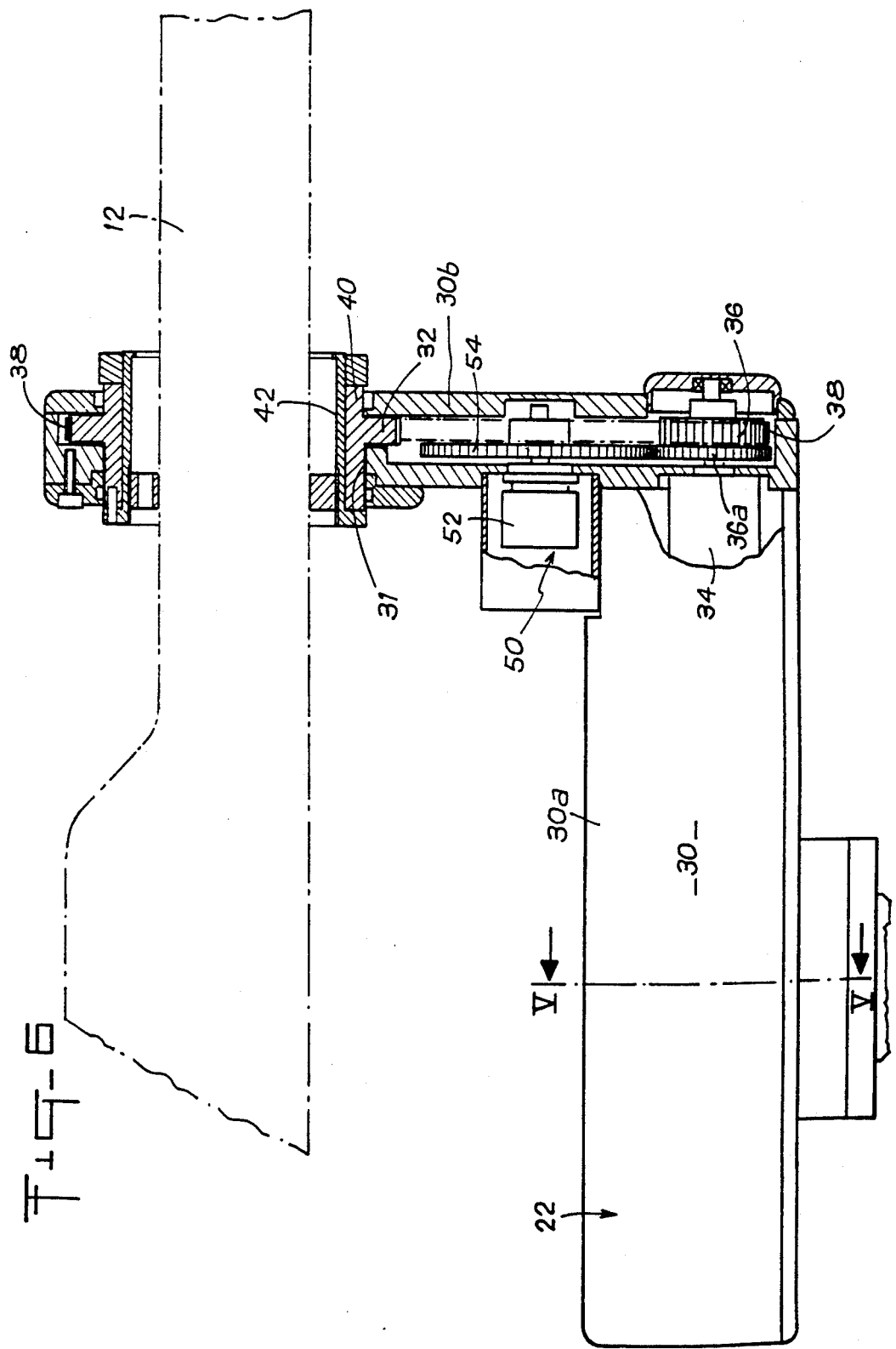

ARM HAVING AN END MOVABLE IN TRANSLATION, AND THERAPEUTIC TREATMENT APPARATUS CONSTITUTING AN APPLICATION THEREOF

The present invention relates essentially to an arm having an end that is movable in translation, and also to therapeutic treatment apparatus constituting an application thereof.

BACKGROUND OF THE INVENTION

Patent document FR-A-2 502 485 discloses exploration apparatus having a "sound" or probe for ultrasound diagnosis, the apparatus comprising an essentially rigid arm having two ends, a first end which is hinged relative to a support stand via at least one hinge axis, and preferably via at least two hinge axes, and a second end including two perpendicular hinge axes supporting a second arm having a support provided at the end thereof for an exploration probe.

The exploration probe mounted on this arm cannot be moved in translation at the end of the arm, and this constitutes a drawback in the context of certain therapeutic applications, in particular for medical exploration, in particular for transrectal exploration.

Patent document FR-A-2 598 073 filed by the same Applicant also discloses a positioning device for positioning an exploration probe in three dimensions and occupying a limited volume. The positioning device is particularly adapted to locating lithiases for lithotrity.

However, that device makes no provision for moving the exploration probe in translation and this limits its application in therapy, in particular for transrectal exploration.

An object of the present invention is to solve the novel technical problem consisting in providing a positioning device for positioning an instrument in three dimensions and also enabling said instrument to move in translation.

Another object of the present invention is to solve the novel technical problem consisting in providing a positioning device for positioning an instrument in three dimensions and offering maximum freedom in positioning said instrument in three dimensions, the positioning device being simple in design, easy to manufacture, and relatively cheap on an industrial scale.

Another object of the invention is to solve the novel technical problem consisting in providing a positioning device for positioning in three dimensions an instrument including an exploration probe, and suitable, in particular, for performing echographical exploration, in particular transrectally, in a manner which is extremely simple, effective, and reliable.

Using the positioning device of the invention for positioning in three dimensions, it is possible to position any type of exploration probe, and in particular a probe for radiographic exploration, particularly using X-rays.

These technical problems are solved for the first time simultaneously by the present invention.

SUMMARY OF THE INVENTION

Thus, in a first aspect, the present invention provides a positioning device for positioning an instrument in three dimensions, the device comprising at least one arm which is essentially rigid having a first end and a second end, the second end being hinged relative to a support stand via at least one hinge axis, and said instrument being mounted on a support which is connected to the second end of the arm via at least one hinge axis, wherein said instrument comprises an exploration probe and said support for the instrument comprises a device for motion in translation enabling the instrument comprising the exploration probe to be moved in translation relative to the second end of the arm, making it possible to perform exploration for each of the translation positions.

In an advantageous embodiment of the invention, the positioning device comprises two arms hinged to each other by at least one hinge, together with a hinge at each of their free ends, giving a total of at least three hinges.

In another variant of the invention, said positioning device includes locking means for locking the hinges simultaneously.

In yet another variant embodiment, said positioning device in which the hinges include moving parts and stationary parts is characterized in that the locking means provide temporary locking by means of relative displacement between the moving parts and the stationary parts of the hinges, and are of the pneumatic or the hydraulic type, in particular.

In another embodiment, said locking means include at least one continuous inside passage enabling a pneumatic or a hydraulic fluid under pressure to pass inside the positioning device when locking is activated, with the arms then being constituted by tubes.

In another advantageous embodiment of the invention, the above-mentioned translation device comprises a stationary part fixed to the hinge at the second end of the arm via a link member, and a moving part movable in translation relative to the fixed part, the moving part supporting the instrument, or vice versa.

In another particularly advantageous embodiment of the invention, the moving part includes means for rotating the instrument, thereby enabling the instrument to move in rotation.

According to a particular characteristic of the invention, the above-mentioned means for rotating the instrument include a declutching member enabling the instrument to be rotated manually.

According to another advantageous characteristic of the device of the invention, the moving part is L-shaped, with one branch thereof moving in translation relative to the stationary parts of the translation device, while its other branch supports the instrument, advantageously in rotary manner.

In a preferred embodiment of the positioning device of the invention, at least one of the hinges, and preferably all of the hinges, is/are ball-and-socket type hinges.

In an advantageous embodiment, the ball-and-socket type hinge at the second end of the arm is the opposite way round, such that the arm is fixed both at its first end and its second end to the normally moving ball part of said ball-and-socket type hinges.

According to another particularly preferred characteristic of the invention, at least some of the sockets of the ball-and-socket hinges have their axes of symmetry at respective acute angles of inclination relative to the general axes of their arms; said angles of inclination advantageously lying in the range 20° to 65°, preferably lying in the range 35° to 60°, and still more preferably, being about 55°.

According to another advantageous characteristic of the invention, the angle of inclination between the socket of the last ball-and-socket type hinge at the second end of the arm and the link member linking it to the stationary part of the translation device is different from that of the other ball-and-socket type hinges.

In a second aspect, the present invention also provides therapeutic treatment apparatus including a positioning device as defined above for positioning an instrument in three dimensions.

In an advantageous embodiment of this therapeutic treatment apparatus, the above-mentioned instrument is an exploration instrument, in particular for providing a display, and in particular an echographic probe, preferably of the transrectal type, for transrectal exploration, and advantageously for exploring the prostate transrectally. This probe may also be a radiographic exploration probe, in particular for use with X-rays.

It will thus be understood that all of the above-mentioned decisive technical advantages are obtained, thus making it possible, in particular, to provide displacement in translation of an instrument supported by the positioning device while maintaining the maximum degrees of freedom for positioning the instruments in an arbitrary position in three dimensions.

BRIEF DESCRIPTION OF THE DRAWINGS

An embodiment of the invention is described by way of example with reference to the accompanying drawings, in which:

FIG. 4 is a section showing details on an enlarged scale of one of the ball-and-socket type hinges of the invention;

FIG. 6 is a section on line VI—VI of FIG. 1.

DETAILED DESCRIPTION

Figure 1:
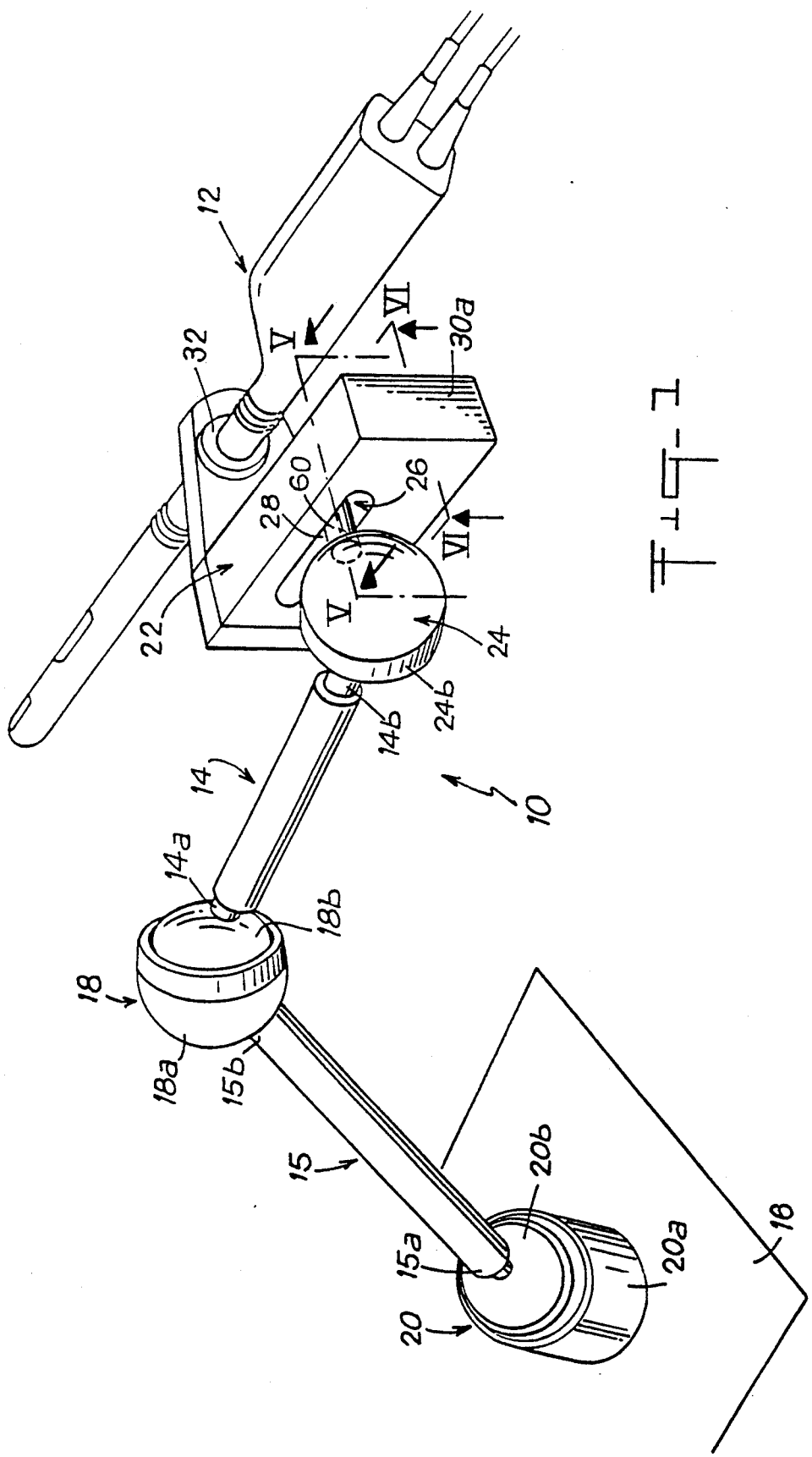
FIG. 1 is a diagrammatic perspective view of the essential parts of a presently preferred embodiment of a positioning device for three dimensional positioning of an instrument such as an exploration probe, and in particular a probe of the echographic type, which device is suitable for use in therapeutic treatment apparatus, and in particular apparatus for hyperthermal treatment, particularly of the prostate.
Figure 2:
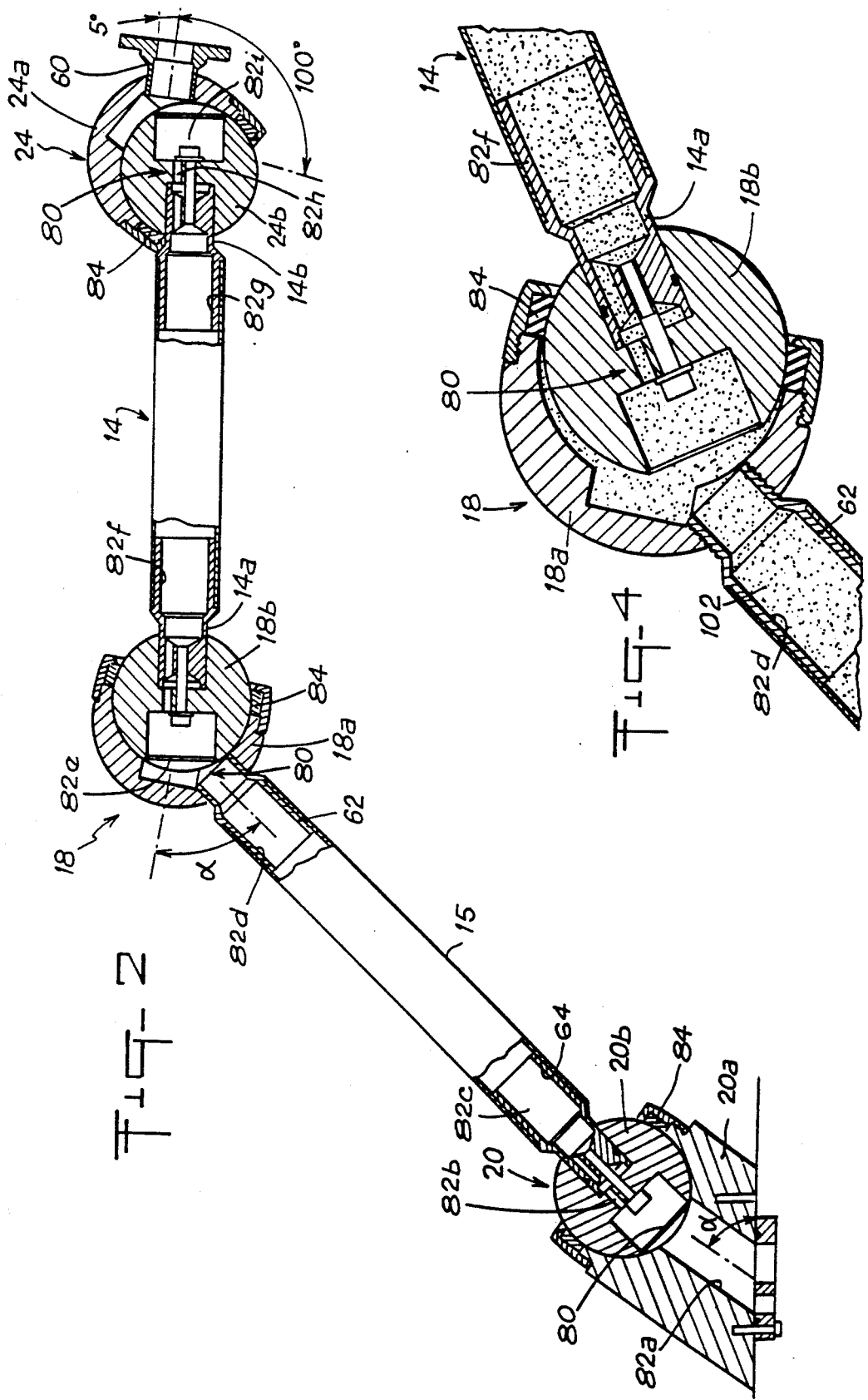
FIG. 2 is a fragmentary longitudinal section showing the ball-and-socket type hinges of the positioning device shown in FIG. 1, with its device for providing motion in translation being removed.
Figure 3:
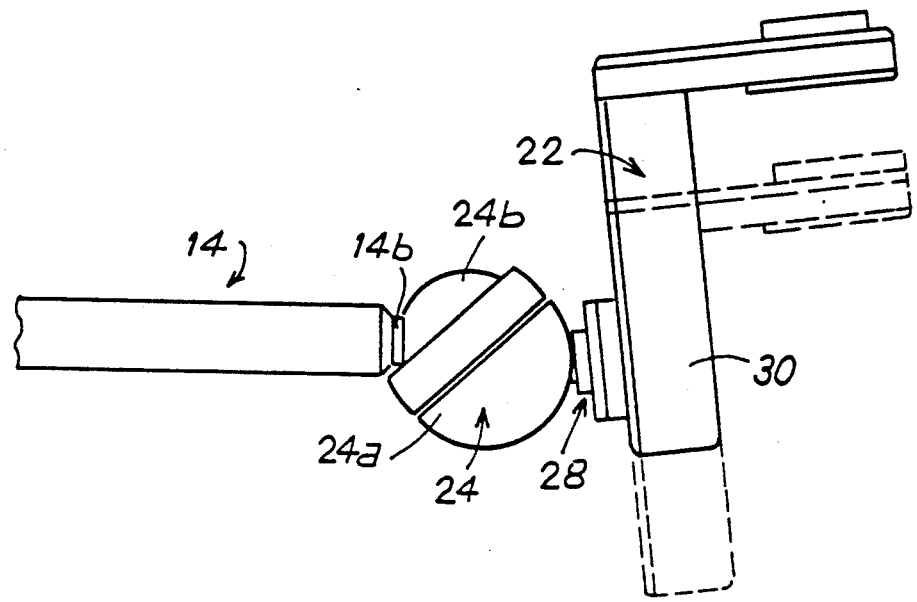
FIG. 3 is a plan view of the device for providing motion in translation showing it in two different translation positions, thus showing how the instrument supported by the device may be moved in translation.

With reference more particularly to FIGS. 1, 2, and 3, a positioning device of the invention for providing positioning in three dimensions is given an overall reference numeral 10 and serves to position an instrument 12 in three dimensions, the instrument being constituted, for example, by an exploration probe and in particular a probe of the echographic or radiographic type, in particular for use with X-rays. The positioning device 10 comprises an essentially rigid arm 14 having a first end 14a and a second end 14b. The first end 14a is hinged relative to a support stand 16 about at least one hinge axis 18, 20, and preferably via at least two hinge axes (18, 20). In addition, the instrument 12 is mounted on a support 22 which is connected to the second end 14b of the arm 14 via at least one hinge axis 24.

According to the present invention, this positioning device is further characterized in that the support 22 for the instrument 12 includes a device 26 for providing motion in translation (shown in greater detail in the section of FIG. 5) and serving to move the instrument 12 in translation relative to the second end 14b of the arm 14.

Figure 5:
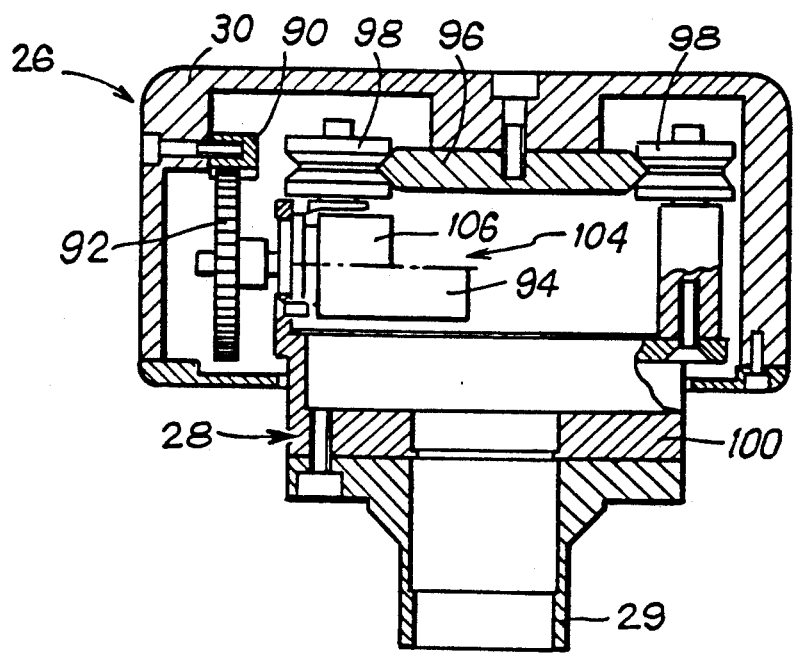
FIG. 5 is a section on line V—V of FIG. 1.

In an advantageous embodiment of the invention, this device 26 for providing motion in translation comprises a stationary part 28 fixed to the hinge 24 at the second end 14b of the arm 14 via a link member 29 and a moving part 30 which is movable in translation relative to the stationary part 28, the moving part 30 supporting the instrument 12 (see FIG. 5).

The moving part 30 may be moved in translation relative to the stationary part 28 by any mechanical system well known to the person skilled in the art. For example, the mechanical system may be constituted by a rack system 90 meshing with a pinion 92 on a drive motor 94 mounted on a support piece 100, which is U-shaped for example, and which forms a portion of the stationary part 28. For example, this support piece 100 may also support wheels 98 disposed on either side of a guide rail 96 fixed to the moving part 30, thereby providing accurate guidance of the motion in translation of the moving part 30.

Translation measurement means 104 may also be provided to measure the translation distance of the moving part 30. For example, this translation measurement means may comprise a potentiometer type encoder 106 as is well known to the person skilled in the art.

In a preferred embodiment of the invention, the moving part 30 includes means 32 (more clearly visible in FIG. 6) for rotating the instrument 12 which is shown in dot-dashed lines.

These means 32 for rotating the instrument may, for example, comprises a rotary drive motor 34 acting via a system comprising a toothed wheel 36 co-operating with a drive component 38 such as a toothed belt which rotates a toothed wheel 40. The toothed wheel 40 includes a central orifice 42 coaxial therewith and in which the instrument 12 is inserted, which instrument may be constituted, for example, by a probe for exploration by means of a display, in particular a probe of the ultrasonic type for echographic exploration.

The rotary drive means 32 may include a clutch member for enabling the instrument 12 to be rotated manually. In this case, the clutch member is constituted merely by the toothed belt drive system 38 in combination with the motor 34. It will be understood that when the probe 12 is rotated manually, then the wheel 40 supporting the instrument 12 is likewise rotated manually, together with the belt 38 and the drive wheel 36 of the motor 34 in entirely free manner.

According to yet another particularly advantageous embodiment of the device of the invention, the device includes rotation measuring means 50 for measuring the rotary displacement of the means 32, and in particularly of the wheel 40. For example, this measurement means 50 may comprise a potentiometer 52 provided with a toothed wheel 54 which also meshes with a toothed wheel 36a constrained to rotate with the wheel 36 of the motor 34, thereby making it possible to calculate the rotary displacement of the wheel 40 and thus of the instrument 12 on the basis of the number of turns through which the wheel 54 rotates, as is well known to the person skilled in the art.

According to another particularly advantageous embodiment of the invention, the moving part 30 is L-shaped as can clearly be seen in FIG. 1 and in FIG. 6, with one branch 30a thereof moving in translation relative to the stationary part 28 and with the other branch 30b thereof supporting the instrument 12. Because of the L-shape, this other branch extends substantially perpendicularly to the branch 30a. This other branch 30b includes a through orifice 31 whose axis is substantially perpendicular to said other branch 30b, and thus substantially parallel to the branch 30a, and the toothed wheel 40 and the instrument 12 are mounted coaxially in said orifice 31. It will thus be understood that the axis of rotation of the instrument 12 is parallel to the branch 30a, and this constitutes an advantageous structural characteristic of the invention.

According to another presently preferred feature of the positioning device of the invention, at least some of the hinges 18, 20, and 24 are of the ball-and-socket type. In this case, all of the hinges 18, 20, and 24 are of the ball-and-socket type.

In a particular embodiment, as shown, the hinge 24 at the second end 14b of the arm 14 is of the opposite way round to the hinge 18 at the first end 14a of the arm. In the preferred embodiment where all of the hinges 18, 20, and 24 are of the ball-and-socket type, these hinges comprise respectively a stationary part or "socket" (respectively referenced 18a, 20a, and 24a) which is essentially in the form of a truncated sphere, together with a moving part or "ball" which is essentially spherical in shape (and respectively referenced 18b, 20b, and 24b), with the part 24b being clearly visible in FIG. 2.

Since the hinge 24 at the second end 14b of the arm 14 is the opposite way round, its "stationary" socket 24a is its part which actually moves and which supports the stationary part 28 of the device 22 for motion in translation which is fixed thereto by a link member 60.

According to another particularly advantageous characteristic of the invention, the ball-and-socket type hinges 18, 20, 24 are designed in such a manner that the link member such as 60, 62, or 64 in each socket respectively referenced 24a, 28a, or 20a takes up an acute angle of inclination α relative to the axis of symmetry of the fixed part. This angle of inclination α may be different for hinge axis 24 at the second end 14b of the arm 14.

Advantageously, this angle of inclination α lies in the range 20° to 65°, and more preferably in the range 35° to 65°. A particularly preferred angle of inclination is about 55°, as shown.

According to another advantageous characteristic of the invention, a second arm 15 is provided, with the positioning device then comprising a total of not less than three hinges 18, 20, and 24, as shown. The first end 15a of the second arm 15 may be connected to the hinge 20, and the second end 15b may be connected to the hinge 18 which it has in common with the first arm 14.

Because of this structure, a particularly simple positioning device is obtained providing a maximum degree of freedom and in which the instrument 12 is movably mounted by means of the displacement device 22.

In addition, locking means 80 may be provided for locking the hinges 18, 20, and 24 in position. These locking means 80 provide temporary locking by relative displacement between the stationary and the moving parts of the hinges and they are, in particular, of the pneumatic or of the hydraulic type. The locking means 80 constitute an invention independent from the positioning device and they are claimed for themselves.

In a particularly advantageous embodiment, the locking means 80 comprise at least one continuous inside passage 82a to 82i enabling a pneumatic or a hydraulic fluid to pass inside the positioning device 10, with the arms 14 and 15 then being constituted by tubes. The fluid is put under pressure when locking is activated. The pneumatic or hydraulic fluid is naturally conveyed by conventional feed means (not shown).

These feed means preferably feed the pneumatic or hydraulic fluid under pressure 102, which pressure preferably lies in the range 4 bars to 7 bars.

A sealing ring 84 may advantageously be provided towards the free end of each socket 18a, 20a, 24a of each of hinge 18, 20, 24, thereby also providing friction between the stationary and the moving parts of the hinges.

To do this, a sealing ring 84 may be made of a material which is different in nature from the material used for the moving parts of the hinge, thereby increasing friction. For example, sealing ring 84 may be made of PVC while the balls such as 18b, 20b, and 24b is made of a plastic material such as an acetal resin, e.g. polyoxymethylene (POM).

It will thus readily be understood that the complete structure as shown in FIGS. 1 to 6 constitutes an integral part of the invention and therefore forms an integral part of the present description.

The invention naturally covers all means constituting technical equivalence of the means described, and various combinations thereof.

This structure makes it possible to lock the ball-and-socket hinges simultaneously, which is most practical, and allows the instrument 12 to be positioned accurately.

We claim:

1. A positioning device for use in three dimensional positioning of a support having an instrument for use with a therapeutic treatment apparatus, the device comprising a stand, at least one substantially rigid arm having a first end and a second end, a first hinge means for securing the first end to said stand for movement about at least one hinge axis, a second hinge means for securing said support to the second end of said at least one arm for movement about at least one hinge axis, and means for moving said support in translation relative to the second end of said at least one arm for enabling said instrument to be moved in translation relative to said second end of said at least one arm.

2. A device according to claim 1, wherein said at least one arm comprises first and second arms and further comprising a third hinge means moveable about at least one hinge axis for securing said first and second arms to each other, said support being secured to the free end of said first arm.

3. A device according to claim 2, further comprising locking means for simultaneously locking said first, second and third hinges thereby restricting movement of said hinges about their respective axes.

4. A device according to claim 3, wherein each hinge means includes a moving part and a stationary part, and wherein the locking means comprises means for effecting relative movement between the moving parts and the stationary parts and wherein said means for effecting movement are of the pneumatic or the hydraulic type.

5. A device according to claim 4, wherein said first and second arms comprise tubes having internal passages which accommodate a pneumatic or hydraulic fluid under pressure for effecting said relative movement between said stationary parts and said moving parts.

6. A device according to claim 2, wherein said first, second and third hinges each comprises a ball-and-socket type joint and wherein at least some of the sockets of said ball-and-socket joints have their axes of symmetry at acute angles of inclination relative to the axis of their attached arms, said angle of inclination lying in the range of 20° to 65°.

7. A device according to claim 6, wherein the means for moving the support in translation comprises a link member secured at one end to said support and at the other end to the socket at the free end of one of said first arm, and wherein the angle of inclination between said socket and said link member is different from the angle of inclination between the sockets of the other ball-and-socket joints and their attached arms.

8. A device according to claim 6, wherein said angle of inclination is in the range of 35°-60°.

9. A device according to claim 8, wherein said angle of inclination is about 55°.

10. A device according to claim 1, wherein the means for moving said support in translation further comprises means for rotating the support, thereby enabling said instrument mounted on said support to move in rotation and translation.

11. A device according to claim 10, wherein the means for rotating the support includes a declutching member for enabling the support to be rotated manually.

12. A device according to claim 1, wherein at least one of the hinge means, and preferably all of the hinge means, comprise ball-and-socket type joints.

13. A device according to claim 12, wherein the first and second ends of the at least one substantially rigid arm are fixed to the ball portion of the ball-and-socket type joints.

14. A device according to claim 1, further comprising measurement means for measuring the displacement of the instrument at least in translation.

15. A device according to claim 1, wherein said means for moving said support in translation further comprises means for rotating said instrument about its axis.

16. A device according to claim 1, wherein said means for moving said support in translation comprises a link member fixedly secured to one of said second end of at least said one arm and said support and movably secured to the other of said second end of said at least one arm and said support for movement of said support in translation relative to said second end of said at least one arm.

17. A device according to claim 16, wherein the means for moving said support in translation further comprises an L-shaped member with one leg having said link member affixed thereto, or having a slot accommodating said link member, and the other leg supporting said instrument for rotation about its axis.

18. In combination:
a therapeutic treatment apparatus: and
a positioning device for use in three dimensional positioning of a support for carrying an instrument connected to the therapeutic treatment apparatus, said positioning device comprising:
a stand, at least one substantially rigid arm having a first end and a second end:
a first hinge means for securing the first end to said stand for movement about at least one hinge axis;
a second hinge means for securing said support to the second end of said at least one arm for movement about at least one hinge axis; and
means for moving said support in translation relative to the second end of said at least one arm for enabling said instrument to be moved in translation relative to said second end of said at least one arm.

19. The device according to claim 18, wherein said instrument comprises an exploration probe providing a display.

20. The device according to claim 19, wherein said exploration probe comprises a transrectal echographic probe for exploring the prostate transrectally.

* * * * *